United States Patent [19]

Dietz

[11] Patent Number: 5,024,219
[45] Date of Patent: * Jun. 18, 1991

[54] APPARATUS FOR INHALATION THERAPY USING TRIGGERED DOSE OXYGENATOR EMPLOYING AN OPTOELECTRONIC INHALATION SENSOR

[76] Inventor: Henry G. Dietz, 80 Salisbury Ave., Garden City, N.Y. 11530

[*] Notice: The portion of the term of this patent subsequent to May 24, 2005 has been disclaimed.

[21] Appl. No.: 303,739

[22] Filed: Jan. 30, 1989

Related U.S. Application Data

[63] Continuation-in-part of Ser. No. 2,743, Jan. 12, 1987, abandoned.

[51] Int. Cl.⁵ .............................................. A61M 16/00
[52] U.S. Cl. ............................ 128/204.21; 128/204.23
[58] Field of Search ...................... 128/204.18, 204.21, 128/204.23, 204.26, 716, 721; 73/705, 861.42

[56] References Cited

U.S. PATENT DOCUMENTS

| | | | |
|---|---|---|---|
| 1,917,940 | 7/1933 | Heidbrink | 128/205.24 |
| 2,185,069 | 12/1939 | Sholes et al. | 128/205.24 |
| 2,216,183 | 10/1940 | Connell | 128/205.24 |
| 2,382,610 | 8/1945 | Dann | 128/205.23 |
| 2,770,231 | 11/1956 | Falk | 128/205.24 |
| 2,904,035 | 9/1959 | Andreasen | 128/205.24 |
| 3,976,064 | 8/1976 | Wood et al. | 128/204.28 |
| 4,360,247 | 11/1982 | Beasley | 73/705 |
| 4,414,982 | 11/1983 | Durkan | 128/204.26 |
| 4,510,930 | 4/1985 | Garcia | 128/205.24 |
| 4,519,387 | 5/1985 | Durkan et al. | 128/204.26 |

Primary Examiner—Aaron J. Lewis

[57] ABSTRACT

A triggered dose oxygenator using an optoelectronic inhalation sensor to trigger a dose of breathable gas, including oxygen, from one of four possible sources of supply to a human user when the user of the triggered dose oxygenator inhales. The four possible sources of supply are: a large tank of breathable gas, a small tank of breathable gas on a wheeled portable cart, a wall outlet supplied from a bulk storage system of breathable gas, and an oxygen concentrator supplying oxygen from ambient air.

2 Claims, 8 Drawing Sheets

APPARATUS FOR INHALATION THERAPY USING TRIGGERED DOSE OXYGENATOR EMPLOYING AN OPTOELECTRONIC INHALATION SENSOR

This application is a continuation-in-part application of U.S. Ser. No. 07/002,743 filed Jan. 12, 1987 now abandoned for: "Method and Apparatus for Using Triggered Dose Oxygenator for Inhalation Therapy."

BACKGROUND OF THE INVENTION

This invention relates generally and more particularly to using a single triggered dose oxygenator employing an optoelectronic inhalation sensor as an apparatus for inhalation therapy that may be supplied with therapeutic gas from a number of supply sources, such as:

Wall outlet supplying a therapeutic gas (such as oxygen) to a patient in a hospital.

High pressure tank supplying a therapeutic gas (such as oxygen) to a patient at home.

Small tank mounted on a portable cart to be used for portable use.

Oxygen concentrator that manufactures oxygen from ambient air.

This invention also pertains to the apparatus used for measuring and controlling a supply of a flow of therapeutic gas to a triggered dose oxygenator employing an optoelectronic inhalation sensor used for inhalation therapy.

The flow of gas in prior art is normally regulated by using a flowmeter with a variable orifice. In a triggered dose oxygenator using the optoelectronic sensor the flow of gas can not be controlled by a variable orifice for the flow of oxygen is turned on and off by means of an electrically operated solenoid valve. This solenoid valve thus acts as a totally closed or open orifice and makes it impossible to use an orifice as part of the flowmeter for controlling the flow of gas.

This invention overcomes the difficulty by using a variable pressure regulator to overcome this problem of regulating the flow of the therapeutic gas.

An additional function is that a triggered dose oxygenator employing an optoelectronic inhalation sensor is able to trigger a dose of inhalation therapy gas when the optoelectronic inhalation sensor detects inhalation. The dose can be adjusted to correspond to the normal period of inhalation, approximately 30% of the time between breaths, so that no therapeutic gas is delivered during exhalation. This can theoretically save 70% of the therapeutic gas that would normally be used if the therapeutic gas is delivered the full breath time.

Intermittent gas flow has been achieved in the prior art by various means (such as Durkan, U.S. Pat. No. 4,484,578) by using fluidically operated devices, that not only require an electrical power source, but also a gas supply to make the sensor function. The advantages of using an optoelectronic sensor is that it only requires an electrical power source and is more sensitive to the extremely low negative pressure of inhalation and reduces the number of components to achieve lower manufacturing cost.

A triggered dose oxygenator using an optoelectronic sensor also has the advantage over prior art in that a single nasal cannula can be used, not only for sensing, but also for delivering the therapeutic gas.

In the prior art, often two connections to the patient are required; one tube to one nasal passageway to sense inhalation, and a second tube to the other nasal passageway to deliver oxygen.

Another advantage of an optoelectronic sensor over the prior art that uses temperature sensing to detect flow of gases over a heated element is that such sensors are affected by humidity, whereas humidity does not affect an optoelectronic sensor, as it is equipped with an eductor that removes the moisture when a dose of oxygen is delivered. In thermo devices where the entire device is on a micro-chip, moisture can destroy the device or cause great inaccuracies in measuring the flow of gases.

SUMMARY OF THE INVENTION

This invention relates to using an optoelectronic sensor in an apparatus that provides a triggered dose of therapeutic gas when inhalation takes place, and which can be used from a number of supply sources.

The inhalation sensor is connected to a human being or a patient using a nasal cannula, commonly used in hospitals for administering oxygen. A nasal cannula used with an optoelectronic inhalation sensor has a dual function of being used for sensing inhalation and delivering oxygen. In the prior art such dual functions were not possible, and it was necessary to use two cannulas, one for each nostril with a single function assigned to each nostril. One nostril would be used for sensing and the other nostril would be used for receiving the therapeutic gas.

The optoelectronic sensor is a pressure device, and is so constructed that after the sensing function is accomplished, the therapeutic gas is delivered through the optoelectronic sensor in such a manner that it acts as an eductor to remove any accumulated moisture from the sensor.

The apparatus used with the optoelectronic sensor to provide intermittent flow of a therapeutic gas, is dependent on the opening and closing of a solenoid valve to obtain the intermittent flow. Therefore, to regulate the flow of therapeutic gas, the flowmeters used in the prior art that regulate flow by means of a variable orifice can not be used with the apparatus shown in this application, for the opening and closing of the valve makes it impossible to obtain the effect of a variable orifice. The valve functions as a fully open or fully closed orifice and over-rides the effect of the variable orifice.

One of the chief advantages of an apparatus using an optoelectronic sensor for inhalation therapy is that it is suitable for use with different therapeutic gas supplies.

When connected to a small portable tank, the diaphragm used in the optoelectronic sensor is not sensitive to shock or vibration even though it is sensitive to pressures of 0.001 of an ounce per square inch, because the diaphragm when installed is bonded and pre-stressed circumferentially, and is activated only by negative pressure of the nasal inhalation.

The advantage of a single triggered dose oxygenator employing an optoelectronic sensor that is able to operate from different supply sources, is that it can best serve a patient for all his requirements. It can be used in a hospital when the oxygen is supplied from a wall outlet and the patient is confined to bed. It can be transferred to a portable unit when the patient is up and exercising. It can be used from a large supply tank when the patient is on home care. It can also be used when the patient does not require a high oxygen concentration and is able to use an oxygen concentrator that manufactures oxygen from ambient air.

None of the prior art exhibits this ability of multiple use, for they are engineered for a single function.

If fluidic type sensors are used with oxygen concentrators, it is a requirement that they be supplied with a constant flow of gas to power the fluidic circuits. This demand for a constant flow of gas from the supply circuit results in a lower yield of oxygen being obtained from the ambient air. The use of an optoelectronic sensor eliminates the need of a gas power supply, because it only requires an electrical power supply for operation. This results in the intermittent flow of the system giving higher yield of oxygen.

Where the inventor has described the use of this invention for oxygen therapy, it should be understood that other gas could be used. It also should be understood that the invention could be used for application in industrial, aeronautical, subterranean, or under water environments.

DETAILED DESCRIPTION OF THE DRAWINGS

DESCRIPTION OF THE PREFERRED EMBODIMENTS

FIG. 1, 2, 3, and 4 generally illustrate the preferred embodiments of the apparatus for using triggered dose oxygenator employing an optoelectronic inhalation sensor for inhalation therapy.

Figure 1:
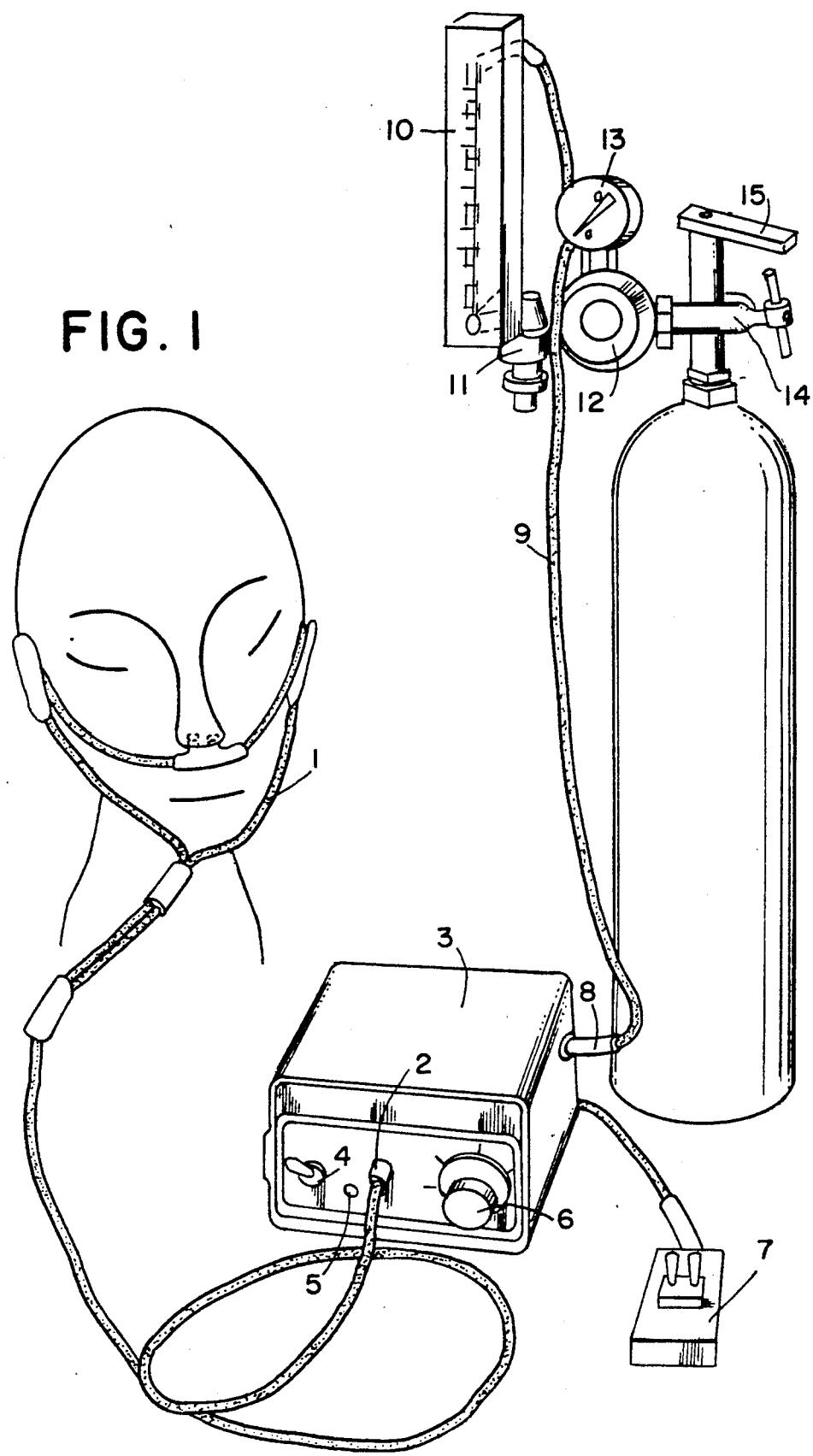
FIG. 1 is a diagrammatic view of the triggered dose oxygenator employing an optoelectronic inhalation sensor being used for inhalation therapy from a fixed tank in isometric projection.

The patient in FIG. 1 is connected to a nasal cannula 1. The cannula 1 is connected to the oxygen outlet 2 of the apparatus for using triggered dose oxygenator employing an optoelectronic inhalation sensor for inhalation therapy.

Figure 8:
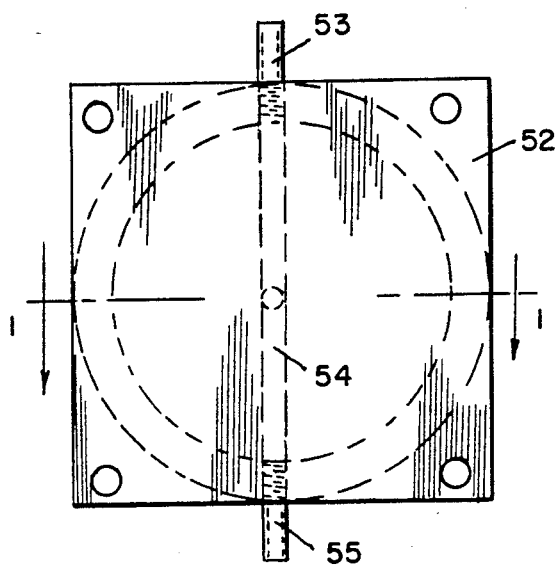
FIG. 8 is a top view of the optoelectronic inhalation sensor according to the invention.
Figure 9:
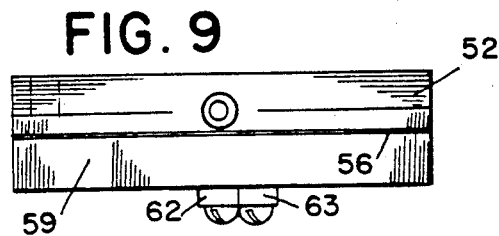
FIG. 9 is a front elevation view of the optoelectronic inhalation sensor according to the invention.
Figure 11:
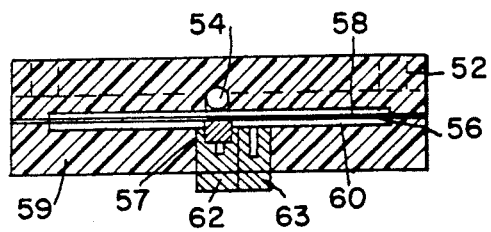
FIG. 11 is a section taken along section line 1—1 of FIG. 5.
Figure 10:
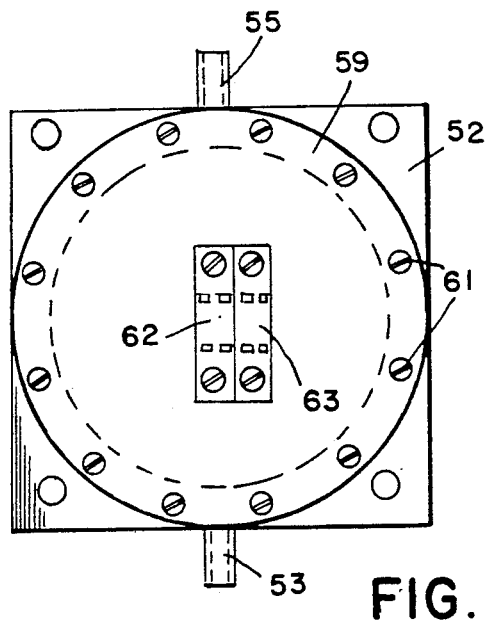
FIG. 10 is a bottom view of the optoelectronic inhalation sensor according to the invention.

FIGS. 8, 9, and 10 generally illustrate a preferred embodiment of an optoelectronic inhalation sensor, which comprises a square housing 52, made of a rectangular opaque electrical non-conductor in cross section FIG. 11, having a circular recess forming a central cavity 58 therein, the square housing 52 having an inlet connection 53, through one end thereof, with a passageway 54, and another outlet connection 55, through the other end of the square housing, both inlet and outlet passages being in direct communication with the central cavity 58 in the square housing 52.

With the flow of inhalation therapy gas into the inlet connection 53, passageway 54 with outlet connection 55 creates a suction in central cavity 58. This slight suction is used as an eductor to clear out any moisture that may have been entrapped in central cavity 58, which, if not removed, could affect operation of the sensor.

The diaphragm 56 is a 0.0005 inch thick polyester film or other equally suitable thin flexible material. The diaphragm 56 is pre-stressed circumferentially and bonded to the surface of the square housing 52 forming a space between the recessed central cavity 58 of housing 52 and the film diaphragm 56. This space changes when a patient inhales, becoming smaller when inhalation takes place.

A clamping disc 59, made of opaque electrical non-conductor material in cross section FIG. 11, having a circular recess forming a central cavity 60, is fastened to the square housing 52 by a plurality of screws 61.

The circular recess forming the lower central cavity 60, is vented to the outside atmospheric pressure. The depth of the circular recess forming the central cavity 60 is minimum, such as 0.005 inch deep, being used to limit the movement of the film diaphragm 56, to prevent the film diaphragm 56 from being stretched when inhalation therapeutic gases with high pressure of 10 pounds per square inch are supplied to the upper central cavity 58. For best operation of the optoelectronic inhalation sensor, the clamping disc 59 should be located at the bottom of the sensor. With changes in temperature, the diaphragm 56 can expand or contract, however, due to the limited depth of the recess, and due to the force of gravity, the diaphragm will always be in close proximity to the set calibration point, which is the point where the film diaphragm 56 is flat with no pressure on either side.

In the center of the clamping disc 59 is a rectangular opening to accept two optoelectronic solid state photon coupled interrupter modules 62 and 63. Module 62 is located in the center of the disc 59, and provides an electrical output when the infrared-opaque vane 57 is moved upward by the film diaphragm 56. The vane 57 is fastened to the center of the film diaphragm 56. Module 63 is located as near as possible to module 62. Module 63 is used as an inactive unit to provide a reference for temperature compensation.

The electrical output of the optoelectronic solid state photon coupled interrupter module 62 occurs when a negative inhalation pressure is applied to the upper central cavity 58 moving the vane 57 upward to allow passage of the infrared light. This puts the module 62 in the same design category as a mechanical precision limit switch, except as the activating vane 57 is blocking light instead of applying force. Thus mechanical wear and deformation effects are eliminated. If mechanical precision limit switches were used it would be necessary to make them mechanically adjustable so that the actuating point of the switches would occur when the diaphragm was displaced a critical distance. Using the optoelectronic module 62, it is possible to adjust the actuating point electrically since adjusting the sensitivity of the detector is equivalent to moving a mechanical precision limit switch in and out from the diaphragm.

The diaphragm 56 will be activated by a small volume of negative inhalation pressure of 0.001 ounce per square inch, which will move the infrared-opaque vane 57 up to signal switching the output from an "Off" state to an "On" state.

The "On" state will trigger a prescribed dose of therapeutic gas at high pressure forcing the diaphragm 56 into the lower central cavity 60, and preparing it for the next inhalation, when the diaphragm 56 will be sucked up into the upper central cavity 58.

Figure 13:
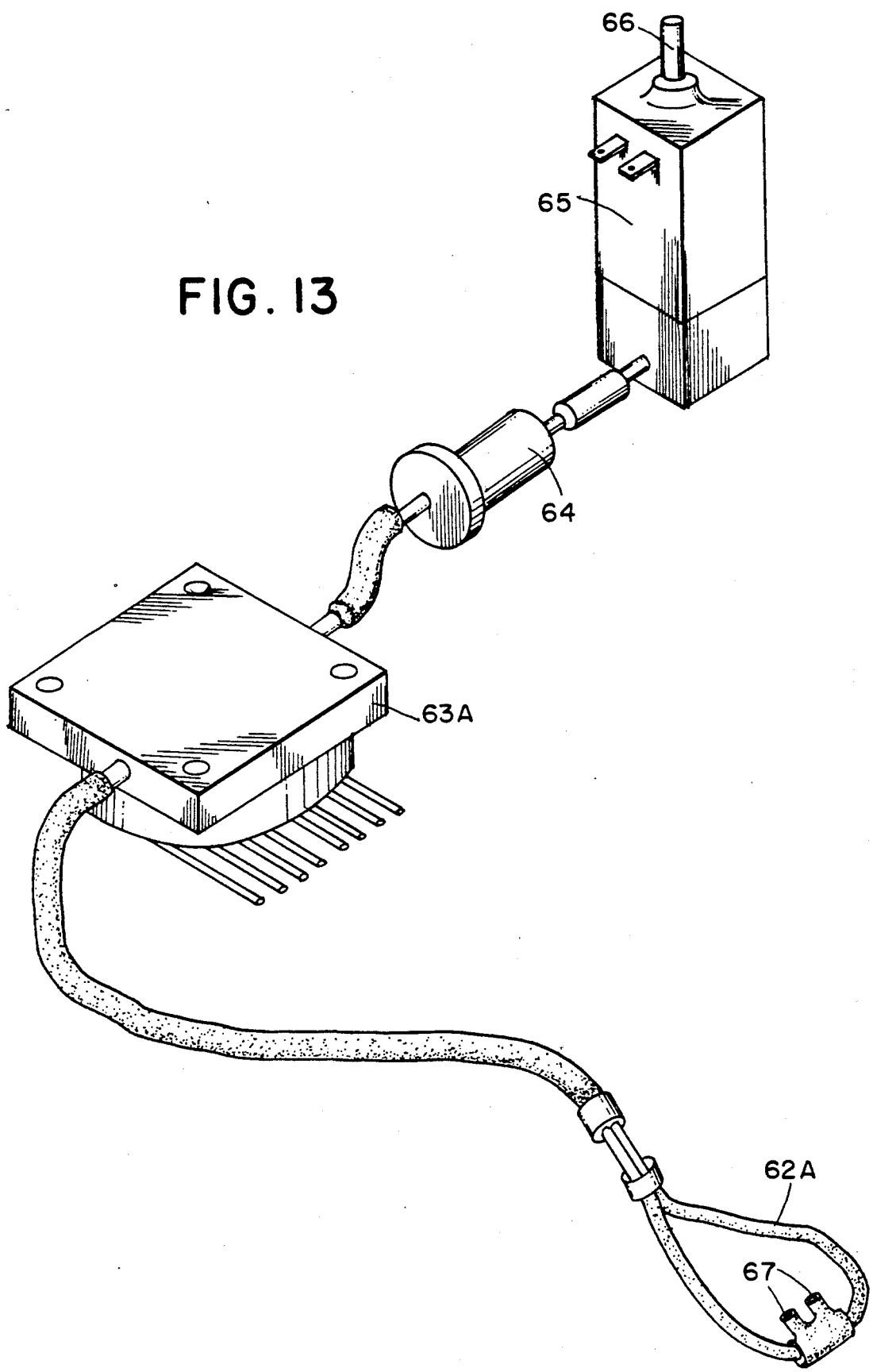
FIG. 13 is a diagrammatic view using the optoelectronic inhalation sensor for inhalation therapy in isometric projection.

FIG. 13 shows one method and apparatus for using an optoelectronic inhalation sensor for inhalation therapy. A cannula 62A, commonly available in hospitals for administering oxygen, is used to connect the flow of air from a patient's nostrils to the optoelectronic inhalation sensor 63A described above, by using the outlet connection 55, FIG. 8.

The filter 64 can be placed as shown on FIG. 13 or inserted between the cannula 62A and optoelectronic inhalation sensor 63A. Its purpose is to prevent any foreign object, that might be present in the gas supply, being inhaled into the patient's lungs.

The optoelectronic inhalation sensor is connected to the normally open solenoid valve 65 by means of appropriate tubing using the inlet connection 53 of the inhalation sensor 63A. The solenoid valve 65 is electrically actuated by low voltage and low current, that can be supplied by an electronic circuit that can be designed to be intrinsically safe (a circuit that is incapable of having a spark or thermal effect that would be capable of causing ignition of flammable or combustible material in the gas being used for inhalation therapy). The connection 66 on the solenoid valve 65 is connected to the supply of gas being used for therapy.

The cannula 62A is adjusted to fit the patient so that the two prongs 67 are inserted into the patient's nostrils. The inhalation flow of air from the patient's nostrils produces a very low pressure or vacuum at the end connected to the inhalation sensor 63A.

The vacuum pressure produced by the patient inhaling is no more than a few thousandths of an ounce per square inch. At the time the patient is exhaling, the electric solenoid valve 65 is electrically activated and shuts off the flow of gas from the therapeutic gas being used. When the patient inhales, the thin film diaphragm 56 is sucked up into the upper central cavity 58, moving the infrared-opaque vane 57 upward to cause an electrical signal to an "On" state. With appropriate electrical circuits as described in this patent specification, a signal is sent for a pre-determined time to cause a flow of therapeutic gas by electrically deactuating the normally open valve 65. In actual practice, it has been found that the flow of air being sucked in by the patient is at a maximum for only a very short period of time, and this peak flow of air vacuum from the patient's nostrils is used to trigger the flow of the therapeutic gas for a pre-set time.

The length of the pre-set time can be adjusted for the correct flow of therapeutic gas for the normal adult rate of 14 to 20 breaths per minute, or for 20 to 40 breaths for babies and toddlers. The respiration rate rises as much as four breaths per minute for every degree of patient's temperature over normal.

The pre-determined time therefore, provides for an intermittent flow of therapeutic gas to the patient. The patient normally inhales approximately for 30% of the time for each breath, with 70% of the breath for exhaling. By setting the pre-set timer to 30% of the breath time, a savings of 70% of the therapeutic gas can be achieved over the normal hospital system of having a constant flow. It is also possible to apply the therapeutic gas at a very early stage of inspiration with a large volume of gas which will reach the alveoli and not waste additional gas that remains in the "dead spaces" such as the pharynx, trachea, and bronchial tubes.

At the time the therapeutic gas flows into the inhalation sensor 63A, high pressure is applied to the diaphragm 56, causing it to be in close contact with the circular recessed surface of the central cavity 60, moving the infrared-opaque vane 57 downward to block the infrared light of the interrupter module 62. Therefore, upon completion of the pre-set time, a signal is sent by the inhalation sensor 63A, to an electrical circuit that actuates the solenoid valve 65 to its closed position and shuts off the flow of therapeutic gas to the inhalation sensor 63A, and the cannula 52A.

Upon completion of the patient's exhaling, the cycle of events will be repeated by the patient again inhaling.

Figure 14:
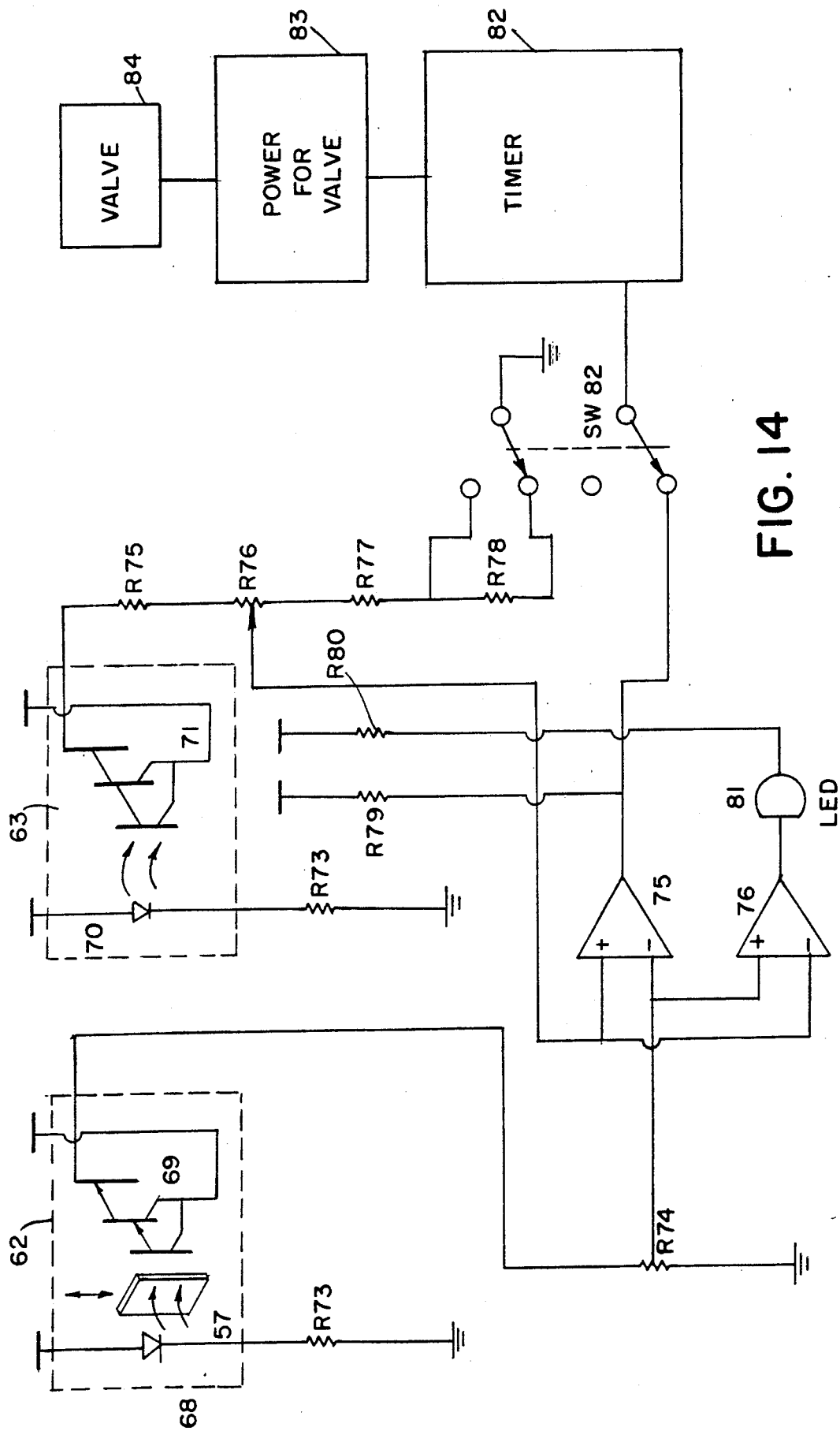
FIG. 14 is a schematic diagram and block diagram for using the optoelectronic inhalation sensor for inhalation therapy.

FIG. 14 generally illustrates a schematic diagram and block diagram of one of the preferred means of electrical circuits used to obtain intermittent flow of the therapeutic gas. The two optoelectronic solid state photon coupled interrupter modules 62 and 63 of FIG. 14 are the same modules 62 and 63 shown in FIG. 8 located in the inhalation sensor 63A.

The module 62 is an interrupter module consisting of a gallium arsenide infrared emitting diode 68 coupled to a silicon darlington connected phototransistor 69, interrupted by the infrared-opaque vane 57. Vane 57 is actuated by the diaphragm 56 of the inhalation sensor 63A.

The module 63 is an interrupter module consisting of a gallium arsenide infrared emitting diode 70 coupled to a silicon darlington connected phototransistor 71, used as a temperature compensater to balance the temperature changes of module 62.

Resistors R72 and R73 are current limiting resistors used for keeping the power dissipation below maximum ratings of the infrared emitting diodes 68 and 70.

The output of the darlington connected phototransistor 69 is fed into the loading resistor R74, which is a potentiometer allowing for a variable adjustable voltage tap to feed into the inverting input of the voltage comparators 75 and 76.

In like manner, the output of the darlington phototransistor 71 is fed into the loading resistors connected in series R75, R76, R77, and R78. Resistor 76 allows for a variable adjustable voltage tap to feed into the non-inverting input of the voltage comparators 75 and 76.

The output voltage of the comparators 75 and 76 will swing from full on to full off when the voltages applied to the inputs differ by only about 0.001 volt. Thus a very small movement of the vane 57 will produce a very small swinging from full off to full on with the voltage being applied to the output resistor R79 and R80. The LED 81 will be illuminated each time the patient exhales, and extinguished each time the patient inhales. The switch SW82 is used for calibrating the sensor. The switch, as shown in FIG. 14, is positioned for normal operation after calibration has taken place.

Placing switch SW82 in the calibration position results in resistor 78 not being in the output load of the darlington connected phototransistor 71, and in disconnecting the output of the voltage comparator 75. With the switch in the calibration position, the potentiometer R76 is adjusted (with the cannula 62A disconnected) so that the LED 81 is made to just illuminate. This is the position of the potentiometer R76 where the position of the vane 57 will be most sensitive to the movement of the diaphragm 56 when inhalation occurs.

The potentiometer R74 is adjusted so that the LED 81 will be just illuminated when potentiometer R76 is set at the mid point. When the sensor is adjusted for maximum sensitivity, the slightest change in the calibration point will cause undesired oscillation because the high pressure of the triggered dose of therapeutic gas is inadvertently being fed back into the input of the sensor causing parasitic oscillations which could mimic the breathing of the patient.

The applicant's invention deals with this difficulty by providing mechanical and electrical means to offset and prevent significant changes in the calibration point. The diaphragm 56 is affected by gravity and temperature. An increase in temperature will cause the diaphragm to expand and gravity will act to pull the diaphragm downward. This difficulty is overcome by limiting the distance (to a very small distance, such as 0.005 inch) the diaphragm can move to the central cavity 60 of the clamping disc 59.

When the high pressure of the triggered dose of therapeutic gas is applied to the diaphragm 56, the diaphragm 56 is prevented from being stretched beyond its limit of elasticity and beyond the point where the material will expand and return to its original shape only after a time delay. A diaphragm that would be allowed to expand to a point where it would be necessary for it to remember its original shape, with a time delay, would cause a the calibration point and undesirable parasitic oscillations. Temperature changes and aging of the interrupter module 62 could also cause shifting of the calibration point and undesirable parasitic oscillations.

This is overcome in the Dietz invention by using a second interrupter module 63 to obtain the reference voltage for the voltage comparators 75 and 76. The temperature and aging characteristics of the interrupter 62 is compensated for by the identical temperature and aging characteristics of the interrupter 63. Since the calibration point is set at the maximum sensitivity, the slightest change in the balance of the circuit due to shift in the calibration point, would cause the unit to become inoperable. To prevent very small changes of the calibration point from affecting the operation of the sensor, the resistor R78 is added to the output loading resistors R75, R76, and R77 to desensitize the circuit and make it less affected by very slight changes in the calibration point.

Figure 12:
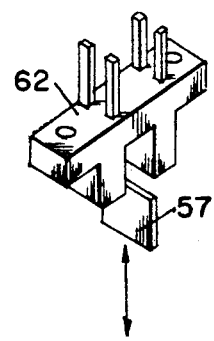
FIG. 12 is a diagrammatic view of the optoelectronic solid state photo coupled interrupter module used in the optoelectronic inhalation sensor in isometric projection.

When the calibration switch SW82 is positioned as shown in FIG. 12, the output of the voltage comparator 75 is fed into a timing circuit 82. The timing circuit 82 will be triggered by the patient's inhaling and result in an output that is for a pre-set time interval that provides power for valve 83 to actuate the valve 84, giving the patient a dose of oxygen.

The inhalation sensor 63A can be used to monitor breathing by using widely available known electrical circuits.

The inventor's patent also provides for fail safe operation, a continuous flow of oxygen will be provided in case of failure of the sensor 63A to operate.

An apparatus using the optoelectronic inhalation sensor previously described for inhalation therapy, is designated as a triggered dose oxygenator 3. FIG. 1 generally illustrates a preferred embodiment of this triggered dose oxygenator 3.

The triggered dose oxygenator 3 of FIG. 1 contains within it the optoelectronic inhalation sensor 63A, the filter 64, and the normally open solenoid valve 65 of FIG. 13. Also the triggered dose oxygenator 3 contains within it all of the electrical circuits and block diagrams of FIG. 14. Switch 4 of FIG. 1 is the power switch that supplies the necessary power for the circuits and block diagrams of FIG. 14. The LED (Light Emitting Diode) of FIG. 1 is the LED 81 of the circuit shown in FIG. 14 and is illuminated each time it is triggered by the patient (or human being) inhaling. The length of time it stays illuminated is determined by the pre-set time that the timer 82 of FIG. 14 is set for. The length of time that a dose of the therapeutic gas is set at is controlled by the knob 6 of FIG. 1 that is used to adjust a potentiometer that controls the length of time for the timer shown as block diagram 82 of FIG. 14.

Block diagrams are used for the timer 82, and for the circuit powering the relay 83 since they are well known by those skilled in the art of electronics. Valve 84 of FIG. 14 is the same as the valve 65 of FIG. 13. The interrupter therapeutic gas flows from connection 2 and is the output from the sensor 63A of FIG. 13. The connection 8 of FIG. 1 is directly connected to the connection 66 on the solenoid valve 65 of FIG. 13.

Figure 2:
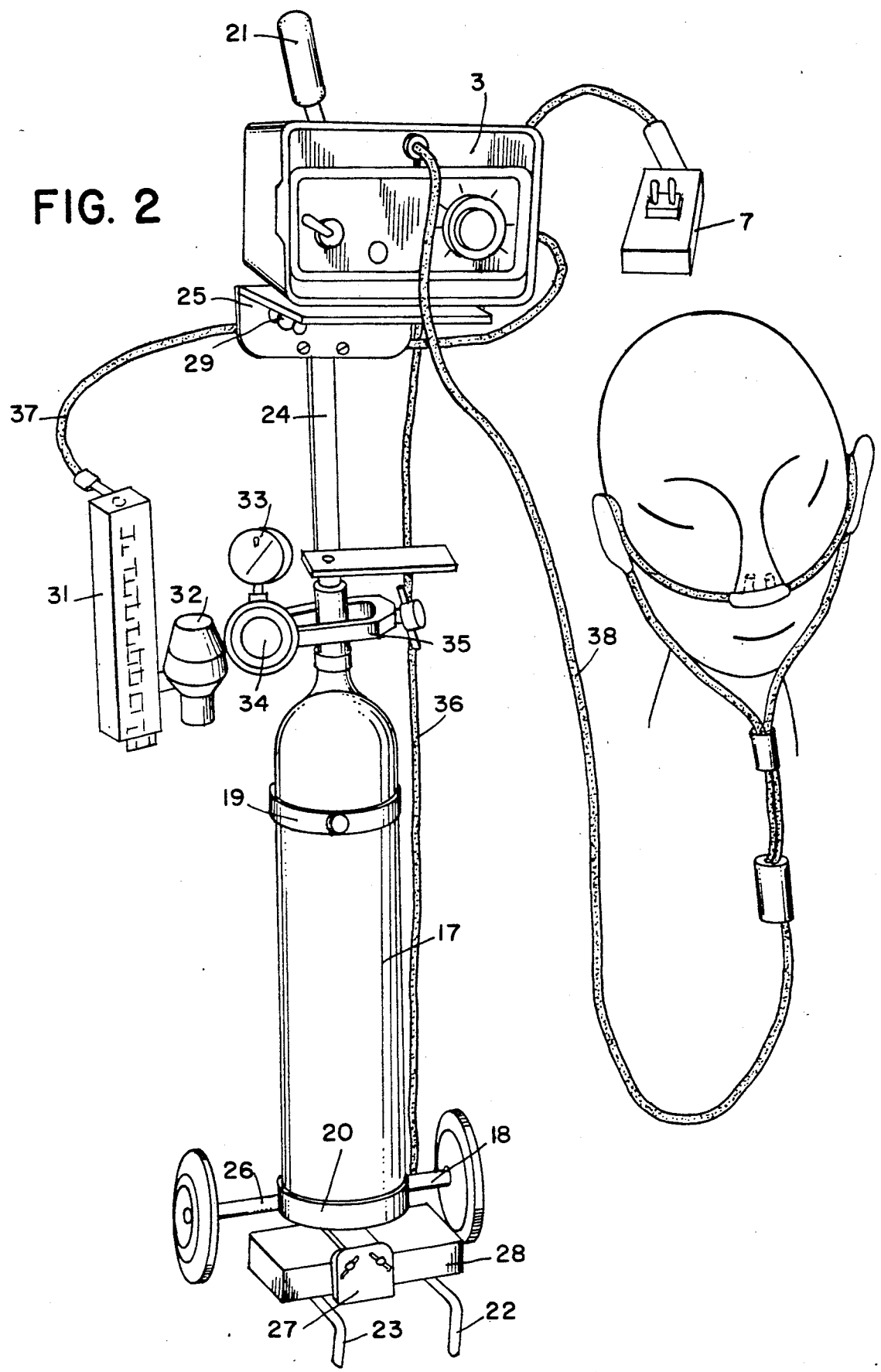
FIG. 2 is a diagrammatic view of the triggered dose oxygenator employing an optoelectronic inhalation sensor being used for inhalation therapy from a portable tank mounted on a cart in isometric projection.

Electric power is low voltage and low current that can be supplied by wall transformer 7 or from any direct current source such as battery 28 of FIG. 2.

The connection 8 of FIG. 1 is connected to the supply of therapeutic gas coming from the flowmeter 10 or 31 of FIG. 2.

The patient in FIG. 1 is connected to a nasal cannula 1 (more commonly used in hospitals for the simple administration of oxygen) for the dual purpose of both receiving a supply of the therapeutic gas and sensing when inhalation occurs. The cannula 1 is connected to the oxygen outlet 2 of the triggered dose oxygenator 3. The oxygenator 3 is set into operation by turning the switch 4 to its on position. The LED (Light Emitting Diode) 5 indicates each time the patient inhales and remains illuminated for the length of time the triggered dose is set. The dose of oxygen given is determined by the setting of the control knob 6. The rate of flow of the oxygen is obtained by turning the power switch 4 to off and adjusting the variable pressure regulator 11 to obtain the rate of flow desired. The rate of flow is indicated by flowmeter 10.

This procedure is used to put the triggered dose oxygenator into operation from any source of therapeutic gas supply.

The oxygen input 8 of FIG. 1 enters oxygenator 3 and is connected by tubing 9 to the flowmeter 10. Flowmeter 10 is connected to the low pressure adjustable pressure regulator 11. The adjustable pressure regulator 11 must be capable of being adjusted to zero pressure. The regulator 11 is connected to a fixed pressure regulator 12. The regulator 12 reduces the tank pressure from a high pressure (such as 2,000 pounds per square inch) to a lower fixed pressure (such as 50 pounds per square inch). The pressure gauge 13 indicates the pressure in tank 16. Pressure regulator 12 is connected to tank 16 by means of a yoke 14.

The triggered dose oxygenator 30 of FIG. 2 is identical to the triggered dose oxygenator 3 of FIG. 1, and operates in like manner.

Figure 5:
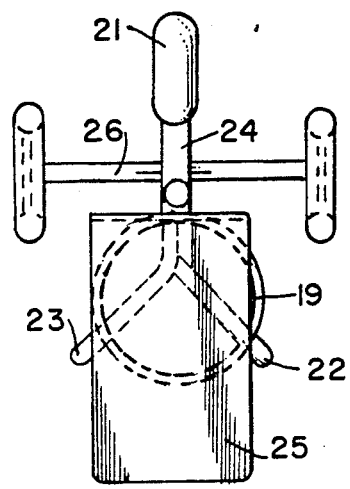
FIG. 5 is a top view of the cart shown in FIG. 2 according to the invention.
Figure 6:
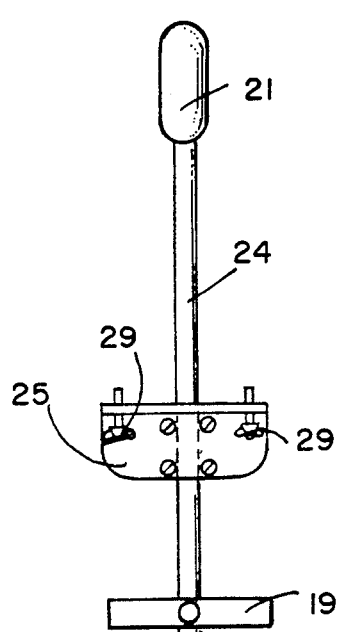
FIG. 6 is a front view of the cart shown in FIG. 2 according to the invention.
Figure 7:
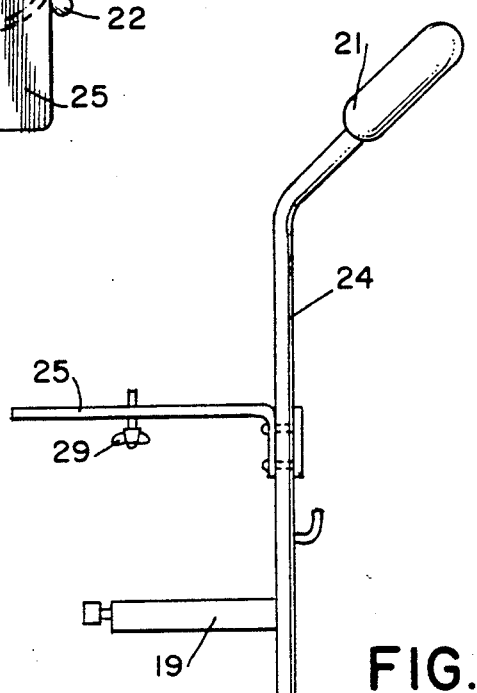
FIG. 7 is a side view of the cart shown in FIG. 2 according to the invention.

However, the triggered dose oxygenator 3 of FIG. 2 and tank 17 are mounted on a wheeled cart 18. The tank 17 is clamped to the cart 18 by means of straps 19 and 20. The cart 18 can be pushed by a patient holding the handle 21. The height of this handle 21 is approximately the height of a common cane used for walking. The oxygenator 3 is fastened to the shelf 25 by means of removable fastener 29. The oxygenator 3 can be easily removed from the shelf 25 so that it would be available for use in FIG. 1. FIG. 5, 6, and 7 are views of the cart 18 of FIG. 2.

Handle 21 of FIG. 2, 5, 6, and 7 is of molded rubber or equivalent material, and it is pushed on to the pipe support 24. Plate 25 is fastened to the pipe by means of four screws and a four hole clamping plate. Straps 19 and 20 are metal and welded to pipe 24. Battery 28 is held in place by clamp 27, which consists of a four hole plate, four screws, and an "L" shaped bracket with tapped holes that is welded to the legs 23 and 22.

The axle 26 is welded to pipe 24 and is provided with means for accepting the pair of wheels to be held in place and rotated.

The portable unit shown in FIG. 2 uses the identical parts shown in FIG. 1, except that the large gas cylinder is replaced by a small tank that is a suitable size and weight for portable use. The power for the unit shown in FIG. 1 is supplied from a wall transformer that has a powered input from 110 or 220 volts AC and an output of low voltage direct current that operates the triggered dose oxygenator 3. This same transformer 7 can be used to operate the triggered dose oxygenator 3, or can be used to recharge the battery 28 for the portable unit shown in FIG. 2. The portable unit of FIG. 2 can thus be operated from a wall outlet (110-220 volts) by use of the transformer 7 or from the battery 28. However, the transformer 7 has the dual function of powering the triggered dose oxygenator 3 of FIG. 2, or being used to recharge the battery 28.

The use of the optoelectronic inhalation sensor makes it possible to detect inhalation negative pressure of 0.001 of an ounce per square inch, and withstand the shock that can occur when the portable unit is rolled over a cobblestone path, because the diaphragm 56 is prestressed circumferentially and bonded to the surface of the square housing 52.

The portable unit of FIG. 2, when in use, will only supply oxygen when the cannula 38 is in use. If the patient removes the cannula 38, no oxygen will flow from tank 17.

Figure 3:
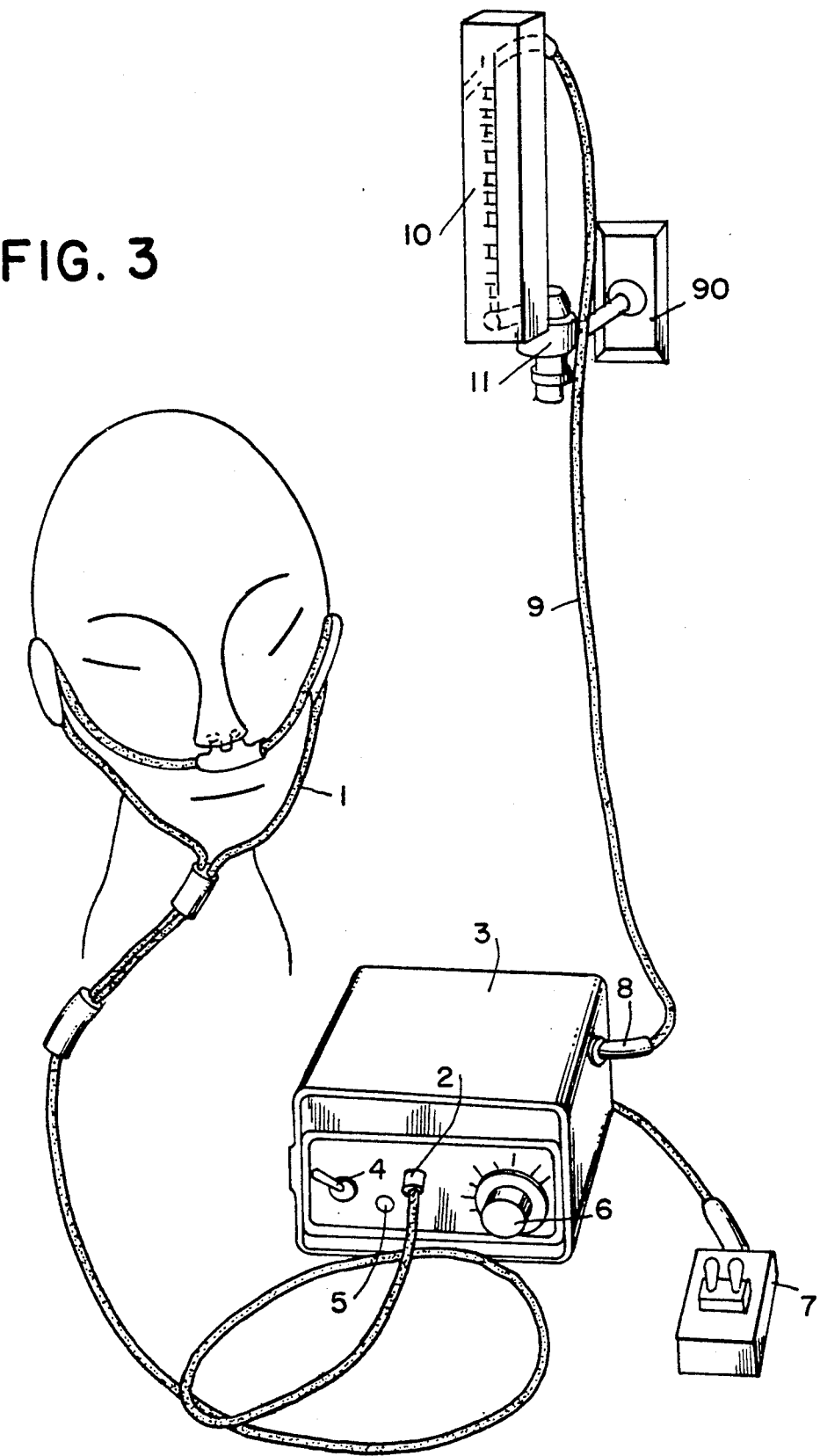
FIG. 3 is a diagrammatic view of the triggered dose oxygenator employing an optoelectronic inhalation sensor being used for inhalation therapy from a wall outlet.

FIG. 3 generally illustrates a preferred embodiment where the triggered dose oxygenator is used from a wall outlet 90 that is supplied from a bulk system that supplies therapeutic gas at a pressure of 50 pounds per square inch. The preferred embodiment of FIG. 3 uses the identical parts shown in FIG. 1, except that the gas cylinder 91 and the fixed gas regulator 12, gauge 13, yoke 14, and wrench 15 are no longer required, for the 50 pound per square inch is acquired directly from the wall outlet. The parts used on FIG. 1 have like numbers when used on FIG. 3 and 4.

At present, most hospitals use flowmeters with variable orifices to control the flow rate. These variable orifice flowmeters will not work with the triggered dose oxygenators 3 of FIG. 1, and 30 of FIG. 2, which require flow to be regulated by pressure regulator 11 of FIG. 1, and 3 of FIG. 2 respectively, which are capable of reducing the 50 pound supply pressure to a value of zero pounds per square inch.

Figure 4:
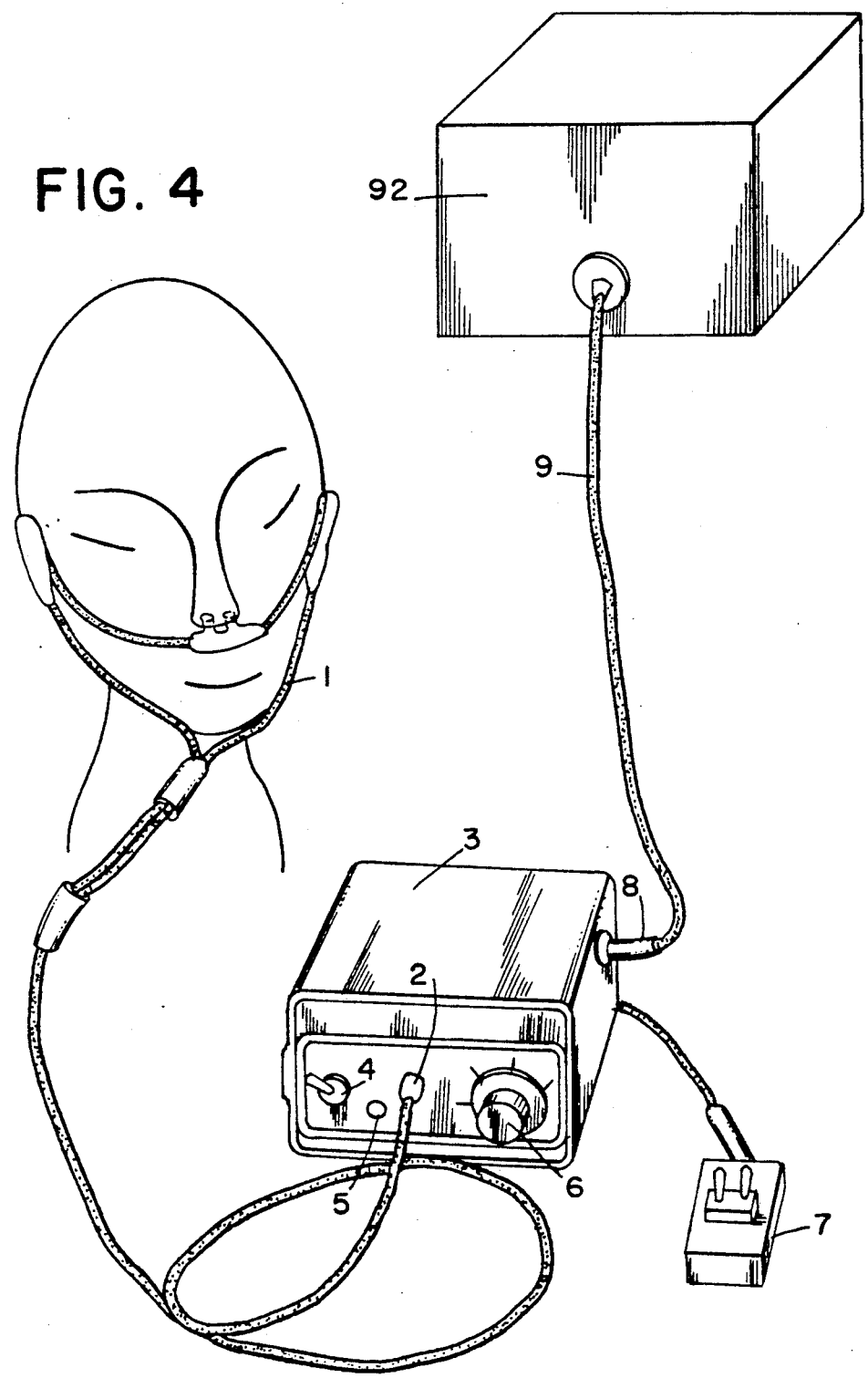
FIG. 4 is a diagrammatic view of the triggered dose oxygenator employing an optoelectronic inhalation sensor being used for inhalation therapy from an oxygen concentrator.

FIG. 4 generally illustrates a preferred embodiment where the triggered dose oxygenator is used with the oxygen enricher or oxygen concentrator 92. Ambient air is pumped either through banks of molecular sieves or a semipermeable membrane, which then preferentially separates oxygen from nitrogen. These devices can operate on household electricity and can deliver about 90% oxygen at a flow rate of 2 liters per minute.

The oxygen concentrators 92 are not portable, but are convenient for continuous oxygen therapy. The triggered dose oxygenator 3 can be used with the oxygen concentrator 92, for the intermittent flow of the oxygenator results in a higher concentration of oxygen than is possible when continuous flow is used.

The preferred embodiment of FIG. 4 uses the identical parts shown in FIG. 1, except that the connection 8 of the triggered dose oxygenator 3 can be directly connected to the oxygen concentrator which usually provides a flow rate of 2 liters per minute.

The intermittent flow devices of prior art, using fluidics, require a constant flow of gas to power their fluidic circuits. This requirement makes it impossible to obtain as high a yield of oxygen as is possible with the triggered dose oxygenator using the optoelectronic inhalation sensor.

While the invention has been particularly shown and described with references to the preferred embodiments thereof, it will be understood by those skilled in the art, that various alterations in form and detail may be made therein without departing from the spirit and scope of the invention.

I claim:

1. An apparatus to trigger a dose of breathable gas, including oxygen, from a tank under high pressure, to a human user when the user inhales, said apparatus comprising:

first pressure regulator means for operable connection to the tank of breathable gas to reduce the pressure of the breathable gas to a second lower pressure which is still above atmospheric pressure;

second pressure regulator means for operable connection to the first pressure regulator means to reduce the pressure of the breathable gas to a third still lower pressure;

flowmeter means for operable connection to the second pressure regulator means to measure the flow of the breathable gas;

optoelectronic inhalation sensor means for operable connection to the flowmeter means to receive the flow of the said breathable gas and to sense when inhalation occurs; said optoelectronic inhalation sensor having a flexible sensing diaphragm at a calibrated position for sensing individual negative pressures developed at each inhalation, optoelectronic means including sensing means for automatically sensing each movement of the diaphragm in response to said negative pressure developed during inhalation, means in said optoelectronic means for developing an electrical signal at each sensed movement of said diaphragm in response to sensing of the individual negative pressure developed at each said inhalation, means for connecting the sensor to a source of a breathable gas, and means to apply said electrical signal to said source of breathable gas for control of supply of said gas to the sensor;

triggered dose oxygenator means for operable connection to the optoelectronic inhalation sensor means and to trigger a dose of the said breathable gas when the optoelectronic sensor means detects inhalation;

cannula means for operable connection to the triggered dose oxygenator means to detect the negative pressure of inhalation of the human user and to deliver the flow of said breathable gas to the human user when inhalation occurs;

electrical power means for operable connection to the triggered dose oxygenator means to supply a direct current from a line voltage wall transformer.

2. An apparatus to trigger a dose of breathable gas according to claim 1, including:

wheeled cart means to transport said apparatus and said tank;

electrical power means for operable connection to the triggered dose oxygenator means to supply a direct current from a battery;

electrical power means for operable connection to the triggered dose oxygenator means to supply a direct current to charge a battery from a line voltage wall transformer.

* * * * *